US007053210B2

(12) United States Patent
Pandey et al.

(10) Patent No.: US 7,053,210 B2
(45) Date of Patent: May 30, 2006

(54) EFFICIENT SYNTHESIS OF PYROPHEOPHORBIDE A AND ITS DERIVATIVES

(75) Inventors: Ravindra K. Pandey, Williamsville, NY (US); Thomas J. Dougherty, Grand Island, NY (US); Alexander J. Pallenberg, Duvall, WA (US)

(73) Assignee: Health Research, Inc., Buffalo, NY (US)

( * ) Notice: Subject to any disclaimer, the term of this patent is extended or adjusted under 35 U.S.C. 154(b) by 128 days.

(21) Appl. No.: 10/613,474

(22) Filed: Jul. 2, 2003

(65) Prior Publication Data

US 2004/0044198 A1     Mar. 4, 2004

Related U.S. Application Data

(60) Provisional application No. 60/393,617, filed on Jul. 2, 2002.

(51) Int. Cl.
 A61B 5/055 (2006.01)
 A61B 10/00 (2006.01)
 C07B 47/00 (2006.01)
 C07F 5/10 (2006.01)
 A61K 31/555 (2006.01)

(52) U.S. Cl. .................. 540/145; 424/9.362; 424/9.61; 534/15; 514/185; 514/410

(58) Field of Classification Search ............... 540/145; 534/15; 514/185, 410; 424/9.1, 9.362, 9.61
See application file for complete search history.

(56) References Cited

U.S. PATENT DOCUMENTS

| | | | |
|---|---|---|---|
| 3,710,795 A | 1/1973 | Higuchi et al. ............. 128/260 |
| 3,817,837 A | 6/1974 | Rubenstein et al. .. 195/103.5 R |
| 3,927,193 A | 12/1975 | Hansen et al. ................. 424/1 |
| RE28,819 E | 5/1976 | Thompson .................. 424/243 |
| 4,044,126 A | 8/1977 | Cook et al. .................. 424/243 |
| 4,328,245 A | 5/1982 | Yu et al. ...................... 424/305 |
| 4,331,647 A | 5/1982 | Goldenberg .................... 424/1 |
| 4,348,376 A | 9/1982 | Goldenberg .................... 424/1 |
| 4,358,603 A | 11/1982 | Yu ................................. 560/2 |
| 4,361,544 A | 11/1982 | Goldenberg .................... 424/1 |
| 4,364,923 A | 12/1982 | Cook et al. .................... 424/46 |
| 4,374,925 A | 2/1983 | Litman et al. ................. 435/7 |
| 4,409,239 A | 10/1983 | Yu ............................... 424/305 |
| 4,410,545 A | 10/1983 | Yu et al. ...................... 424/305 |
| 4,414,209 A | 11/1983 | Cook et al. .................. 424/243 |
| 4,444,744 A | 4/1984 | Goldenberg ................. 424/1.1 |
| 4,468,457 A | 8/1984 | Goldenberg et al. .......... 435/69 |
| 4,474,893 A | 10/1984 | Reading ...................... 436/547 |
| 4,479,895 A | 10/1984 | Auditore-Hargreaves ............. 260/112 B |
| 4,521,762 A | 6/1985 | Kapral ........................ 340/347 |
| 4,522,811 A | 6/1985 | Eppstein et al. ................ 514/2 |
| 4,577,636 A | 3/1986 | Spears ........................ 128/654 |
| 4,624,846 A | 11/1986 | Goldenberg ................. 424/1.1 |
| 4,649,151 A | 3/1987 | Dougherty et al. ......... 514/410 |
| 4,656,186 A | 4/1987 | Bommer et al. ............ 514/410 |
| 4,675,338 A | 6/1987 | Bommer et al. ............ 514/410 |
| 4,693,885 A | 9/1987 | Bommer et al. ........... 424/9.61 |
| 4,753,958 A | 6/1988 | Weinstein et al. .......... 514/410 |
| 4,818,709 A | 4/1989 | Primus et al. .............. 436/518 |
| 4,861,876 A | 8/1989 | Kessel ........................ 540/145 |
| 4,866,168 A | 9/1989 | Dougherty et al. ......... 540/145 |
| 4,878,891 A | 11/1989 | Judy et al. ...................... 604/5 |
| 4,889,129 A | 12/1989 | Dougherty et al. ......... 128/664 |
| 4,916,221 A | 4/1990 | Kumadaki et al. .......... 540/145 |
| 4,925,736 A | 5/1990 | Shikowitz ................... 424/449 |
| 4,932,934 A | 6/1990 | Dougherty et al. ........... 604/21 |
| 4,935,498 A | 6/1990 | Sessler et al. ................ 534/15 |
| 4,946,778 A | 8/1990 | Ladner et al. ............. 435/69.6 |
| 4,957,481 A | 9/1990 | Gatenby ...................... 604/20 |
| 4,968,715 A | 11/1990 | Dougherty et al. .......... 514/410 |
| 4,997,639 A | 3/1991 | Aizawa et al. ................ 424/9 |
| 5,002,962 A | 3/1991 | Pandey et al. .............. 514/410 |
| 5,004,811 A | 4/1991 | Bommer et al. ............ 540/145 |
| 5,015,463 A | 5/1991 | Dougherty et al. .......... 424/7.1 |
| 5,028,594 A | 7/1991 | Carson ........................ 514/23 |
| 5,028,621 A | 7/1991 | Dougherty et al. ......... 514/410 |
| 5,033,252 A | 7/1991 | Carter ......................... 53/425 |
| 5,041,078 A | 8/1991 | Matthes et al. ................ 604/4 |
| 5,051,415 A | 9/1991 | Moran et al. ............... 514/185 |
| 5,052,558 A | 10/1991 | Carter ......................... 206/439 |
| 5,053,006 A | 10/1991 | Watson ......................... 604/52 |
| 5,059,415 A | 10/1991 | Neuwelt ........................ 424/9 |
| 5,062,431 A | 11/1991 | Potter ......................... 128/665 |

(Continued)

FOREIGN PATENT DOCUMENTS

EP        0120054 B1      3/1984

(Continued)

OTHER PUBLICATIONS

Brockmann et al. Partialsynthese Eines Bacteriophaophorbid-C-Methylesters., Jun. 1979. Tetrahedron Letters. No. 23, pp. 2133-2136.*

Smith et al. Purpurinimides as Photosensitizers: Effect of the Presence and Position of the Substituents in the In Vivo Photodynamic Efficacy . . . Jul. 2002. Bioorganic & Medicinal Chemistry Letters 10 pp. 1463-1466.*

(Continued)

*Primary Examiner*—James O. Wilson
*Assistant Examiner*—Mathew L. Fedowitz
(74) *Attorney, Agent, or Firm*—Michael L. Dunn

(57) ABSTRACT

A process for the preparation of pyropheophorbide a and its derivatives, including 3-devinyl-3-(1'-hexyloxy)ethyl-pyropheophorbide-a, otherwise known as HPPH, is provided. The process involves treating chlorin $e_6$, in the form of its trimethyl ester, with a base, followed by heating to give pyropheophorbide a, which is converted to HPPH by treatment with acid, followed by hexyl alcohol under basic conditions.

11 Claims, No Drawings

U.S. PATENT DOCUMENTS

| | | | |
|---|---|---|---|
| 5,066,274 A | 11/1991 | Bommer et al. | 604/20 |
| 5,066,291 A | 11/1991 | Stewart | 606/3 |
| 5,074,632 A | 12/1991 | Potter | 385/31 |
| 5,093,349 A | 3/1992 | Pandey et al. | 514/410 |
| 5,095,030 A | 3/1992 | Levy et al. | 514/410 |
| 5,111,821 A | 5/1992 | Potter | 128/654 |
| 5,145,863 A | 9/1992 | Dougherty et al. | 514/410 |
| 5,171,741 A | 12/1992 | Dougherty | 514/185 |
| 5,173,504 A | 12/1992 | Dougherty | 514/410 |
| 5,190,536 A | 3/1993 | Wood et al. | 606/16 |
| 5,190,966 A | 3/1993 | Dougherty et al. | 514/410 |
| 5,198,460 A | 3/1993 | Pandey et al. | 514/410 |
| 5,205,291 A | 4/1993 | Potter | 128/654 |
| 5,216,012 A | 6/1993 | Morgan et al. | 514/410 |
| 5,219,345 A | 6/1993 | Potter | 606/15 |
| 5,222,795 A | 6/1993 | Hed | 362/32 |
| 5,225,433 A | 7/1993 | Dougherty et al. | 514/410 |
| 5,257,970 A | 11/1993 | Dougherty | 604/20 |
| 5,263,925 A | 11/1993 | Gilmore, Jr. et al. | 604/4 |
| 5,298,018 A | 3/1994 | Narciso, Jr. | 604/21 |
| 5,308,861 A | 5/1994 | Aizawa et al. | 514/410 |
| 5,314,905 A | 5/1994 | Pandey et al. | 514/410 |
| 5,323,907 A | 6/1994 | Kalvelage | 206/531 |
| 5,330,741 A | 7/1994 | Smith et al. | 424/9 |
| 5,344,928 A | 9/1994 | Masuya et al. | 544/37 |
| 5,368,841 A | 11/1994 | Trauner et al. | 424/9 |
| 5,403,308 A | 4/1995 | Wood et al. | 606/17 |
| 5,418,130 A | 5/1995 | Platz et al. | 435/2 |
| 5,430,051 A | 7/1995 | Aizawa et al. | 514/410 |
| 5,441,531 A | 8/1995 | Zarate et al. | 607/90 |
| 5,459,159 A | 10/1995 | Pandey et al. | 514/410 |
| 5,482,698 A | 1/1996 | Griffiths | 424/141 |
| 5,484,803 A | 1/1996 | Richter | 514/410 |
| 5,496,308 A | 3/1996 | Brown et al. | 606/15 |
| 5,498,710 A | 3/1996 | Pandey et al. | 540/145 |
| 5,500,009 A | 3/1996 | Mendes et al. | 607/88 |
| 5,503,637 A | 4/1996 | Kyricos et al. | 607/88 |
| 5,506,255 A | 4/1996 | Smith et al. | 514/410 |
| 5,514,669 A | 5/1996 | Selman | 514/63 |
| 5,525,338 A | 6/1996 | Goldenberg | 424/178.1 |
| 5,532,171 A | 7/1996 | Motsenbocker | 436/533 |
| 5,534,506 A | 7/1996 | Morgan et al. | 514/185 |
| 5,538,945 A | 7/1996 | Pallenberg et al. | 514/6 |
| 5,549,660 A | 8/1996 | Mendes et al. | 607/88 |
| 5,556,612 A | 9/1996 | Anderson et al. | 424/59 |
| 5,567,409 A | 10/1996 | Aizawa et al. | 424/9.363 |
| 5,571,152 A | 11/1996 | Chen et al. | 607/92 |
| 5,580,896 A | 12/1996 | Horwell et al. | 514/419 |
| 5,591,847 A | 1/1997 | Pandey et al. | 540/472 |
| 5,594,136 A | 1/1997 | Sessler et al. | 540/472 |
| 5,599,923 A | 2/1997 | Sessler et al. | 540/145 |
| 5,622,983 A | 4/1997 | Horwell et al. | 514/419 |
| 5,624,798 A | 4/1997 | Yamamoto et al. | 435/6 |
| 5,631,281 A | 5/1997 | Horwell et al. | 514/419 |
| 5,637,311 A | 6/1997 | Pallenberg | 424/434 |
| 5,648,485 A | 7/1997 | Dolphin et al. | 540/474 |
| 5,665,328 A | 9/1997 | Horan et al. | 424/1.17 |
| 5,671,317 A | 9/1997 | Weishaupt et al. | 385/137 |
| 5,688,486 A | 11/1997 | Watson et al. | 424/1.65 |
| 5,697,902 A | 12/1997 | Goldenberg | 604/49 |
| 5,698,405 A | 12/1997 | Goldenberg | 435/7.5 |
| 5,702,432 A | 12/1997 | Chen et al. | 607/88 |
| 5,703,230 A | 12/1997 | Boyle et al. | 540/145 |
| 5,705,518 A | 1/1998 | Richter et al. | 514/410 |
| 5,709,874 A | 1/1998 | Hanson et al. | 424/423 |
| 5,715,837 A | 2/1998 | Chen | 128/899 |
| 5,716,595 A | 2/1998 | Goldenberg | 414/1.49 |
| 5,736,563 A | 4/1998 | Richter | 514/410 |
| 5,741,316 A | 4/1998 | Chen et al. | 607/61 |
| 5,759,542 A | 6/1998 | Gurewich | 424/94.64 |
| 5,766,234 A | 6/1998 | Chen et al. | 607/92 |
| 5,770,619 A | 6/1998 | Richter et al. | 514/410 |
| 5,770,730 A | 6/1998 | Pandey et al. | 540/472 |
| 5,773,977 A | 6/1998 | Dougherty | 324/429 |
| 5,776,093 A | 7/1998 | Goldenberg | 604/20 |
| 5,776,094 A | 7/1998 | Goldenberg | 604/20 |
| 5,776,095 A | 7/1998 | Goldenberg | 604/20 |
| 5,782,896 A | 7/1998 | Chen et al. | 607/88 |
| 5,800,478 A | 9/1998 | Chen et al. | 607/88 |
| 5,814,008 A | 9/1998 | Chen et al. | 604/21 |
| 5,824,080 A | 10/1998 | Lamuraglia | 623/11 |
| 5,827,186 A | 10/1998 | Chen et al. | 600/407 |
| 5,829,448 A | 11/1998 | Fisher et al. | 128/898 |
| 5,831,088 A | 11/1998 | Dolphin et al. | 540/474 |
| 5,832,931 A | 11/1998 | Wachter et al. | 128/898 |
| 5,840,674 A | 11/1998 | Yatvin et al. | 514/2 |
| 5,851,225 A | 12/1998 | Lawandy | 607/88 |
| 5,860,957 A | 1/1999 | Jacobsen et al. | 604/156 |
| 5,864,035 A | 1/1999 | Pandey et al. | 540/472 |
| 5,865,840 A | 2/1999 | Chen | 607/92 |
| 5,876,427 A | 3/1999 | Chen et al. | 607/88 |
| 5,885,557 A | 3/1999 | Lentini | 424/59 |
| 5,886,173 A | 3/1999 | Hemmi et al. | 540/472 |
| 5,900,252 A | 5/1999 | Calanchi et al. | 424/459 |
| 5,913,884 A | 6/1999 | Trauner et al. | 607/88 |
| 5,921,244 A | 7/1999 | Chen et al. | 128/897 |
| 5,942,534 A | 8/1999 | Trauner et al. | 514/410 |
| 5,944,748 A | 8/1999 | Mager et al. | 607/88 |
| 5,945,762 A | 8/1999 | Chen et al. | 310/171 |
| 5,948,433 A | 9/1999 | Burton et al. | 424/448 |
| 5,952,366 A | 9/1999 | Pandey et al. | 514/410 |
| 5,957,960 A | 9/1999 | Chen et al. | 607/92 |
| 5,972,366 A | 10/1999 | Haynes et al. | 424/422 |
| 5,976,535 A | 11/1999 | Fritzberg et al. | 424/182.1 |
| 5,983,134 A | 11/1999 | Ostrow | 604/20 |
| 5,985,307 A | 11/1999 | Hanson et al. | 424/423 |
| 5,985,317 A | 11/1999 | Venkateshwaran et al. | 424/449 |
| 5,997,569 A | 12/1999 | Chen et al. | 607/88 |
| 5,997,842 A | 12/1999 | Chen | 424/1.29 |
| 5,998,597 A | 12/1999 | Fisher et al. | 536/23.1 |
| 6,004,534 A | 12/1999 | Langer et al. | 424/9.321 |
| 6,010,715 A | 1/2000 | Wick et al. | 424/448 |
| 6,015,897 A | 1/2000 | Theodore et al. | 540/474 |
| 6,017,888 A | 1/2000 | Pallenberg et al. | 514/19 |
| 6,022,961 A | 2/2000 | Yamamoto et al. | 536/24.3 |
| 6,024,975 A | 2/2000 | D'Angelo et al. | 424/449 |
| 6,028,099 A | 2/2000 | de Juan, Jr. | 514/434 |
| 6,036,941 A | 3/2000 | Bottiroli et al. | 424/9.6 |
| 6,039,975 A | 3/2000 | Shah et al. | 424/473 |
| 6,048,359 A | 4/2000 | Biel | 607/92 |
| 6,048,736 A | 4/2000 | Kosak | 436/536 |
| 6,051,207 A | 4/2000 | Klaveness et al. | 424/9.1 |
| 6,051,702 A | 4/2000 | Bird et al. | 540/122 |
| 6,060,082 A | 5/2000 | Chen et al. | 424/450 |
| 6,063,108 A | 5/2000 | Salansky et al. | 607/89 |
| 6,063,777 A | 5/2000 | Hikida et al. | 514/183 |
| 6,071,495 A | 6/2000 | Unger et al. | 424/9.51 |
| 6,080,160 A | 6/2000 | Chen et al. | 606/72 |
| 6,084,717 A | 7/2000 | Wood et al. | 359/629 |
| 6,090,788 A | 7/2000 | Lurie | 514/23 |
| 6,092,531 A | 7/2000 | Chen et al. | 128/899 |
| 6,096,066 A | 8/2000 | Chen et al. | 607/88 |
| 6,096,289 A | 8/2000 | Goldenberg | 424/1.49 |
| 6,100,893 A | 8/2000 | Ensz et al. | 345/420 |
| 6,103,751 A | 8/2000 | Pandey et al. | 514/410 |
| 6,107,466 A | 8/2000 | Hasan et al. | 530/351 |
| 6,117,862 A | 9/2000 | Margaron et al. | 514/185 |
| 6,120,751 A | 9/2000 | Unger | 424/9.51 |
| 6,123,923 A | 9/2000 | Unger et al. | 424/9.52 |
| 6,124,342 A | 9/2000 | Okamoto et al. | 514/432 |
| 6,131,570 A | 10/2000 | Schuster et al. | 128/203.26 |
| 6,138,681 A | 10/2000 | Chen et al. | 128/899 |
| 6,139,865 A | 10/2000 | Friend et al. | 424/441 |
| 6,152,951 A | 11/2000 | Hashimoto et al. | 607/92 |

| | | | |
|---|---|---|---|
| 6,156,506 A | 12/2000 | Yamamoto et al. ............ 435/6 |
| 6,162,213 A | 12/2000 | Stewart ........................ 606/10 |
| 6,162,242 A | 12/2000 | Peyman ....................... 607/88 |
| 6,167,301 A | 12/2000 | Flower et al. ................ 604/20 |
| 6,176,842 B1 | 1/2001 | Tachibana et al. ............ 604/22 |
| 6,187,030 B1 | 2/2001 | Gart et al. .................... 607/93 |
| 6,210,425 B1 | 4/2001 | Chen ............................. 607/88 |
| 6,217,869 B1 | 4/2001 | Meyer et al. ............. 424/178.1 |
| RE37,180 E | 5/2001 | Mori et al. .................. 514/410 |
| 6,232,295 B1 | 5/2001 | Kayyem et al. ............... 514/44 |
| 6,238,426 B1 | 5/2001 | Chen ............................. 607/88 |
| 6,242,477 B1 | 6/2001 | Okamoto et al. ........... 514/432 |
| 6,253,872 B1 | 7/2001 | Neumann ................... 181/210 |
| 6,256,533 B1 | 7/2001 | Yuzhakov et al. ........... 604/21 |
| 6,261,595 B1 | 7/2001 | Stanley et al. .............. 424/449 |
| 6,264,914 B1 | 7/2001 | Klaveness et al. ......... 424/1.65 |
| 6,267,983 B1 | 7/2001 | Fujii et al. .................. 424/448 |
| 6,268,120 B1 | 7/2001 | Platz et al. ..................... 435/2 |
| 6,271,359 B1 | 8/2001 | Norris et al. .............. 536/23.1 |
| 6,273,904 B1 | 8/2001 | Chen et al. .................... 607/88 |
| 6,274,552 B1 | 8/2001 | Tamarkin et al. ............. 514/12 |
| 6,281,611 B1 | 8/2001 | Chen et al. .................. 310/171 |
| 6,307,147 B1 | 10/2001 | Bird et al. ................... 136/263 |
| 6,316,652 B1 | 11/2001 | Steliou ........................ 556/42 |
| 6,319,273 B1 | 11/2001 | Chen et al. .................... 607/88 |
| 6,319,488 B1 | 11/2001 | Licha et al. ................ 424/9.6 |
| 6,331,175 B1 | 12/2001 | Goldenberg ................ 604/522 |
| 6,331,744 B1 | 12/2001 | Chen et al. .................. 310/171 |
| 6,344,050 B1 | 2/2002 | Chen ........................... 607/88 |
| 6,350,431 B1 | 2/2002 | Snow et al. ................. 424/9.6 |
| 6,387,350 B1 | 5/2002 | Goldenberg ............... 424/1.57 |
| 6,406,297 B1 | 6/2002 | Raymond et al. ............. 434/15 |
| 6,416,531 B1 | 7/2002 | Chen ............................. 607/89 |
| 6,454,789 B1 | 9/2002 | Chen et al. .................... 607/88 |
| 6,482,517 B1 | 11/2002 | Anderson ............... 428/402.24 |
| 6,489,314 B1 | 12/2002 | Ashley et al. .............. 514/183 |
| 6,495,585 B1 | 12/2002 | Bellnier et al. ............. 514/410 |
| 6,498,945 B1 | 12/2002 | Alfheim et al. ............. 600/407 |
| 6,500,816 B1 | 12/2002 | Ekimoto et al. ............ 514/185 |
| 6,511,971 B1 | 1/2003 | Gorun ........................ 514/183 |
| 6,514,995 B1 | 2/2003 | Zaleski et al. .............. 514/332 |
| 6,515,113 B1 | 2/2003 | Raymond et al. ........... 534/15 |
| 6,520,669 B1 | 2/2003 | Chen et al. .................. 362/545 |
| 6,524,552 B1 | 2/2003 | Klaveness et al. ......... 424/1.85 |
| 6,525,088 B1 | 2/2003 | Nagano et al. ............. 514/452 |
| 6,527,759 B1 | 3/2003 | Tachibana et al. .......... 604/500 |
| 6,534,040 B1 | 3/2003 | Pandey et al. .............. 424/362 |
| 6,540,980 B1 | 4/2003 | Blumenthal et al. ........ 424/9.34 |
| 6,554,853 B1 | 4/2003 | Chen ........................... 607/88 |
| 6,559,374 B1 | 5/2003 | Lindsey et al. ............. 136/263 |
| 6,566,517 B1 | 5/2003 | Miura et al. ................. 540/145 |
| 6,569,846 B1 | 5/2003 | Scherz et al. ............... 514/185 |
| 6,572,839 B1 | 6/2003 | Sugita et al. ................ 424/9.5 |
| 6,580,228 B1 | 6/2003 | Chen et al. ............. 315/185 R |
| 6,602,274 B1 | 8/2003 | Chen ........................... 607/88 |
| 6,624,187 B1 | 9/2003 | Pandey et al. .............. 514/410 |
| 6,657,351 B1 | 12/2003 | Chen et al. .................. 310/171 |
| 2001/0022970 A1 | 9/2001 | Dees et al. ................ 424/178.1 |
| 2002/0033192 A1 | 3/2002 | Lindsey et al. ............. 136/263 |
| 2002/0049247 A1 | 4/2002 | Chen ........................... 514/410 |
| 2002/0087205 A1 | 7/2002 | Chen ........................... 607/88 |
| 2002/0127224 A1 | 9/2002 | Chen ....................... 424/130.1 |
| 2002/0127230 A1 | 9/2002 | Chen ....................... 424/178.1 |
| 2002/0128303 A1 | 9/2002 | Bellnier et al. ............. 514/410 |
| 2002/0198576 A1 | 12/2002 | Chen et al. .................... 607/88 |
| 2003/0018371 A1 | 1/2003 | Chen ........................... 607/88 |
| 2003/0030342 A1 | 2/2003 | Chen et al. .................. 310/102 |
| 2003/0109813 A1 | 6/2003 | Chen ............................. 601/2 |
| 2003/0114434 A1 | 6/2003 | Chen et al. .................. 514/185 |
| 2003/0167033 A1 | 9/2003 | Chen ........................... 604/20 |
| 2003/0208249 A1 | 11/2003 | Chen ........................... 607/88 |
| 2004/0044197 A1 | 3/2004 | Pandey et al. .............. 540/140 |
| 2004/0044198 A1 | 3/2004 | Pandey et al. .............. 540/145 |

FOREIGN PATENT DOCUMENTS

| | | |
|---|---|---|
| EP | 0161606 B1 | 11/1985 |
| EP | 0243929 B1 | 11/1987 |
| EP | 0423195 B1 | 4/1991 |
| EP | 0425566 B1 | 5/1991 |
| EP | 0450149 B1 | 10/1991 |
| EP | 0468997 B1 | 2/1992 |
| EP | 0510007 B1 | 10/1992 |
| EP | 0682956 B1 | 11/1995 |
| EP | 0765152 B1 | 4/1997 |
| EP | 1110963 A2 | 6/2001 |
| EP | 1131100 B1 | 9/2001 |
| EP | 1146046 A2 | 10/2001 |
| EP | 1164136 A1 | 12/2001 |
| EP | 1238666 A2 | 9/2002 |
| EP | 1256586 A1 | 11/2002 |
| EP | 1334748 A1 | 8/2003 |
| JP | 4218002 | 7/1992 |
| JP | 6105921 | 4/1994 |
| JP | 2001335578 | 4/2001 |
| JP | 200220389 | 1/2002 |
| JP | 2002325853 | 11/2002 |
| JP | 2003146989 | 5/2003 |
| WO | 8401382 A1 | 4/1984 |
| WO | 9000392 A1 | 1/1990 |
| WO | 9000895 A1 | 2/1990 |
| WO | 9012573 A1 | 11/1990 |
| WO | 9110474 A1 | 7/1991 |
| WO | 9313769 A1 | 7/1993 |
| WO | 9409851 A1 | 5/1994 |
| WO | 9427594 A1 | 12/1994 |
| WO | 9505214 A1 | 2/1995 |
| WO | 9532206 A1 | 11/1995 |
| WO | 9535085 A1 | 12/1995 |
| WO | 9637255 A1 | 11/1996 |
| WO | 9639144 A1 | 12/1996 |
| WO | 9701559 A1 | 1/1997 |
| WO | 9732520 A1 | 9/1997 |
| WO | 9732885 A1 | 9/1997 |
| WO | 9804317 A1 | 2/1998 |
| WO | 9806456 A1 | 2/1998 |
| WO | 9808565 A1 | 3/1998 |
| WO | 9814243 A1 | 4/1998 |
| WO | 9824371 A1 | 6/1998 |
| WO | 9824510 A1 | 6/1998 |
| WO | 9832491 A1 | 7/1998 |
| WO | 9832492 A1 | 7/1998 |
| WO | 9832493 A1 | 7/1998 |
| WO | 9846130 A1 | 10/1998 |
| WO | 9850034 A1 | 11/1998 |
| WO | 9856302 A1 | 12/1998 |
| WO | 9918879 A1 | 4/1999 |
| WO | 9920346 A1 | 4/1999 |
| WO | 9939769 A1 | 8/1999 |
| WO | 9952565 A1 | 10/1999 |
| WO | 9958149 A1 | 11/1999 |
| WO | 9966988 A1 | 12/1999 |
| WO | 9967248 A1 | 12/1999 |
| WO | 9967249 A1 | 12/1999 |
| WO | 0015296 A1 | 3/2000 |
| WO | 0036983 A1 | 6/2000 |
| WO | 0041725 A2 | 7/2000 |
| WO | 0041726 A3 | 7/2000 |
| WO | 0041727 A1 | 7/2000 |
| WO | 0041768 A1 | 7/2000 |
| WO | 00/61584 A1 | 10/2000 |
| WO | 0103770 A1 | 1/2001 |
| WO | 0105316 A1 | 1/2001 |
| WO | 0115694 A1 | 3/2001 |
| WO | 0143825 A1 | 6/2001 |
| WO | 0151087 A2 | 7/2001 |
| WO | 01/74398 A1 | 10/2001 |

| | | |
|---|---|---|
| WO | 0178216 A1 | 10/2001 |
| WO | 0178458 A1 | 10/2001 |
| WO | 0198708 A1 | 12/2001 |
| WO | 0217690 A1 | 2/2002 |
| WO | 02/098882 A1 | 12/2002 |
| WO | 03029494 A1 | 4/2003 |
| WO | 03/050082 A2 | 6/2003 |
| WO | 03052793 A2 | 6/2003 |
| WO | 03056407 A2 | 7/2003 |
| WO | 03061696 A2 | 7/2003 |
| WO | 2004/002476 A2 | 1/2004 |
| WO | 2004/005289 A2 | 1/2004 |

OTHER PUBLICATIONS

Smith et al. Partial Synthesis of Optically Pure Methyl Bacteriopheophorbides c and d from Methyl Pheophorbide a.Jan. 1980. Journal of Organic Chemistry, 45 pp. 2218-2224.*

Mironov. Synthesis and Properties of New Chlorin and Bacteriochlorin Photsensitizers. SPIE 1996. vol. 2625 pp. 23-32.*

Rungta et al. Purpurinimides as Photosensitizers: Effect of the Presence and Position of the SUbstituents in the In Vivo Photodynamic Efficacy. Biorganic & Medicinal Chemistry Letters. 2000. vol. 10 pp. 1463-1466.*

Smith et al. Partial Syntheses of Optically Pure Methyl Bacteriopheophorbides c and d from Methyl Pheophorbide a. Journal of Organic Chemistry. 1980 45 pp. 2218-2224.*

Bellnier et al., "Population pharmacokinetics of the photodynamic therapy agent 2-[1-hexyloxyethyl]-2-devinyl pyropheophorbide-a in cancer patients", *Cancer Res.*, 63(8):1806-1813 (2003).

Bellnier et al., "Design and construction of a light-delivery system for photodynamic therapy", *Med. Phys.*, 26(8):1552-1558 (1999).

Bellnier et al., "The time course of cutaneous porphyrin photosensitization in the murine ear", *Photochemistry and Photobiology*, 49(3):369-372 (1989).

Bellnier et al., "Murine pharmacokinetics and antitumor efficacy of the photodynamic sensitizer 2-[1-hexyloxyethyl]-2-devinyl pyropheophorbide-a", *J Photochem Photobiol B*. 20(1):55-61 (1993).

Bellnier et al., "The validation of a new vascular damage assay for photodynamic therapy agents", *Photochem Photobiol.*, 62(5):896-905 (1995).

Bellnier et al. "Protection of murine foot tissue and transplantable tumor against Photofrin-II-mediated photodynamic sensitization with WR-2721", *Journal of Photochemistry and Photobiology B. Biology* 4:219-225 (1989).

Bellnier et al. "An assay for the quantitation of Photofrin in tissues and fluids", *Photochem Photobiol.* 66(2):237-244 (1997).

Bellnier et al., "Distribution and elimination of Photofrin II in mice", *Photochemistry and Photobiology* 50(2):221-228 (1989).

Bellnier et al., "Membrane lysis in Chinese hamster ovary cells treated with hemtoporphyrin derivative plus light", *Photochem Photobiol.* 36(1):43-47 (1982).

Bellnier et al., "A preliminary pharmacokinetic study of intravenous Photofrin in patients", *J Clin Laser Med Surg.*, 14(5):311-4 (1996).

Bellnier et al., "Haematoporphyrin derivative photosensitization and gamma-radiation damage interaction in Chinese hamster ovary fibroblasts", *Int J Radiat Biol Relat Stud Phys Chem Med.* 50(4):659-664 (1986).

Bernstein et al., "Photofrin photodynamic therapy for treatment of AIDS-related cutaneous Kaposi's sarcoma", *AIDS*, 13(13):1697-1704 (1999).

Box et al., "Radical ion saturation in some sulfur compounds x-irradiated at 4.2 degrees" *K. Radiat Res.* 51(1):10-14 (1972).

Boyle et al., "Photobleaching of photofrin II as a means of eliminating skin photosensitivity", *Photochemistry and Photobiology*, 46(6):997-1001 (1987).

Brasseur et al., "Photodynamic activities and skin photosensitivity of the bis(dimethylthexylsiloxy)silicon 2,3-naphthalocyanine in mice", *Photochemistry and Photobiology* 62(6):1058-1065 (1995).

Brennan et al., "Preparation of Bispecific Antibodies by Chemical Recombination of Monoclonal Immunoglobulin $G_1$ Fragments",*Science*, 229:81-83 (1985).

Bugelski et al., "Autoradiographic distribution of hematoporphyrin derivative in normal and tumor tissue of the mouse", *Cancer Res.*, 41(11 Pt 1):4606-4612 (1981).

Chen et al., "Effect of meso-substituents on the osmium tetraoxide reaction and pinacol-pinacolone rearrangement of the corresponding vic-dihydroxyporphyrins", *J Org Chem.* 66(11):3930-3939 (2001).

Chen et al., "Bacteriopurpurinimides: highly stable and potent photosensitizers for photodynamic therapy", *J. Med. Chem.* 45:255-258 (2002).

Derwent Abstract Accession No. 9432597, for Japanese Patent Application JP 2003146989 published May 21, 2003, entitled "Pyropheophorbides and their use in photodynamic therapy".

Dimitroff et al., "Anti-angiogenic activity of selected receptor tyrosine kinase inhibitors, PD166285 and PD173074: implications for combination treatment with photodynamic therapy", *Investigational New Drugs*, 17:121-135 (1999).

Dissous et al.,*Schistosoma Mansoni* Surface Antigen Defined by a Rat Monoclonal IgG2a ,*J. Immunol*. 129:2232-2234 (1982).

Doiron et al., "Fluorescence bronchoscopy for detection of lung cancer", *Chest*, 76(1):27-32 (1979).

Dougherty TJ, "Transannular peroxides as radiation sensitizers", *Radiat Res.*, 55(1):101-108 (1973).

Dougherty TJ, "A brief history of clinical photodynamic therapy development as Roswell Park Cancer Institute", *J Clin Laser Med Surg.* 14(5):219-221 (1996).

Dougherty TJ, "Use of hematoporphyrin in photodynamic therapy", *J Photochem Photobiol B*. 8(4):439 (1991).

Dougherty TJ, "Photosensitizers: therapy and detection of malignant tumors", *Photochemistry and Photobiology* 45(6):879-889 (1987).

Dougherty TJ, "Activated dyes as antitumor agents", *J Natl Cancer Inst.* 52(4):1333-1336 (1974).

Dougherty TJ, "Photodynamic therapy", *Photochem Photobiol.*, 58(6):895-900 (1993).

Dougherty TJ, "Photodynamic Therapy: Part II", *Seminars in Surgical Oncology*, 11:333-334 (1995).

Dougherty TJ, "Photodynamic therapy: status and potential", *Oncology (Huntingt)*. 3(7):67-73; Discussion 74, 77-78 (1989).

Dougherty TJ, "Photoradiation therapy for cutaneous and subcutaneous malignancies", *J Invest Dermatol*. 77(1):122-124 (1981).

Dougherty TJ, "Photodynamic therapy (PDT) of malignant tumors", *CRC Critical Reviews in Oncology/Hematology* 2(2):83-116 (1984).

Dougherty TJ, "Photoradiation therapy", *Urology*, 23(3 Suppl):61-64 (1984).

Dougherty TJ, "Photosensitization of malignant tumors", *Seminars in Surgical Oncology* 2:24-37 (1986).

Dougherty TJ, "Variability in hematoporphyrin derivative preparations", *Cancer Res.* 42(3):1188 (1982).

Dougherty TJ, "Photoradiation therapy for bronchogenic cancer", *Chest*, 81(3):265-266 (1982).

Dougherty TJ, "Photodynamic therapy—new approaches", *Seminars in Surgical Oncology* 5:6-16 (1989).

Dougherty TJ, "Hematoporphyrin as a photosensitizers of tumors", *Photochem Photobiol.* 38(3):377-379 (1983).

Dougherty TJ, "Photodynamic therapy", *Adv Exp Med Biol.*, 193:313-328 (1985).

Dougherty TJ, "Photodynamic therapy", *Clinics in Chest Medicine*, 6(2):219-236 (1985).

Dougherty TJ, "An update on photodynamic therapy applications", *J Clin Laser Med Surg.* 20(1):3-7 (2002).

Dougherty TJ, "Studies on the structure of porphyrins contained in Photofrin II" *Photochem Photobiol.*, 46(5):569-573 (1987).

Dougherty et al., "Energetics and efficiency of photoinactivation of murine tumor cells containing hematoporphyrin", *Cancer Research* 36:2330-2333 (1976).

Dougherty et al., "Photoradiation therapy. II. Cure of animal tumors with hematoporphyrin and light", *Journal of the National Cancer Institute*, 55(1):115-121 (1975).

Dougherty et al., "Photoradiation therapy for the treatment of malignant tumors", *Cancer Res.* 38(8):2628-2635 (1978).

Dougherty et al., "Photodynamic Therapy," *Journal of the National Cancer Institute*, 90(12):889-905 (1998).

Dougherty TJ, "Hematoporphyrin derivative for detection and treatment of cancer", *J Surg Oncol.* 15(3):209-210 (1980).

Dougherty et al., "Photoradiation therapy—clinical and drug advances", *Adv Exp Med Biol.* 160:3-13 (1983).

Dougherty et al., "Photoradiation in the treatment of recurrent breast carcinoma", *J Natl Cancer Inst.*, 62(2):231-237 (1979).

Dougherty et al. "Cutaneous phototoxic occurrences in patients receiving Photofrin", *Lasers Surg Med.* 10(5):485-488 (1990).

Dougherty et al., "Interstitial photoradiation therapy for primary solid tumors in pet cats and dogs", *Cancer Res.* 41(2):401-404 (1981).

Dougherty, "Photodynamic therapy in gastrointestinal cancer", *Lasers in Surgery and Medicine* 12:114 (1992).

Dougherty et al., "Characterization of intra-tumoral porphyrin following injection of hematoporphyrin derivative or its purified component", *Photochemistry and Photobiology*, 46(1):67-70 (1987).

Dougherty et al., "The role of the peripheral benzodiazepine receptor in photodynamic activity of certain pyropheophorbide ether photosensitizers: albumin site II as a surrogate marker for activity", *Photochem Photobiol.*, 76(1):91-97 (2002).

Dougherty TJ, "An overview of the status of photoradiation therapy", *Prog Clin Biol Res.* 170:75-87 (1984).

Dougherty et al., "Photodynamic therpay", *Eur J Cancer.* 28A(10):1734-1742 (1992).

Dougherty et al., "The structure of the active component of hematoporphyrin derivative", *Prog Clin Biol Res.*, 170:301-314 (1984).

Dougherty et al., "Of what value is a highly absorbing photosensitizer in PDT?" *J Photochem Photobiol B.*, 8(2):223-225 (1991).

Douglass et al., "Intra-abdominal applications of hematoporphyrin photoradiation therapy", *Adv Exp Med Biol.*, 160:15-21 (1983).

Farrell et al., "A diffusion theory model of spatially resolved, steady-state diffuse reflectance for the noninvasive determination of tissue optical properties in vivo", *Med Phys.*, 19(4):879-888 (1992).

Fingar et al., "Drug and light dose dependence of photodynamic therapy: a study of tumor cell clonogenicity and histologic changes", *Photochem Photobiol.*, 45(5):643-650 (1987).

Flock et al., "Monte Carlo Modeling of Light Propagation in Highly Scattering Tissues—I: Model Predictions and Comparison with Diffusion Theory," *IEEE Transactions on Biomedical Engineering*, 36(12):1162-1168 (1989).

Flock et al., "Monte Carlo Modeling of Light Propagation in Highly Scattering Tissues—II:Comparison with Measurements in Phantoms," *IEEE Transactions on Biomedical Engineering*, 36(12):1169-1173 (1989).

Fukuzumi et al., "Photochemical and electrochemical porperties of zinc chlorin-C60 dyad as compared to corresponding free-base chlorin-C60, free-base porphyrin-C60, and zinc prophyrin-C60 dyads", *J Am Chem Soc.*, 123(43):10676-10683 (2001).

Glennie et al., "Preparation and Performance of Bispecific $F(ab'\gamma)_2$ Antibody Containing Thioether-Linked Fab'$\gamma$ Fragments",*J. Immunol.*, 139:2367-2375 (1987).

Gomer CJ et al., "Determination of [3H]- and [14C]hematoporphyrin derivative distribution in malignant and normal tissue", *Cancer Res.* 39(1):146-151 (1979).

Graham et al., "Structure-activity relationship of new octaethylporphyrin-based benzochlorins as photosensitizers for photodynamic therapy", *Photochem Photobiol.* 77(5):561-566 (2003).

Gryshuk et al., "A first comparative study of purpurinimide-based fluorinated vs. nonfluorinated photosensitizers for photodynamic therapy", *Photochem Photobiol.*, 76(5):555-559 (2002).

Gryzch et al., "In Vitro and In Vivo Effector Function of Rat IgG2a Monoclonal Anti-*S. Masoni* Antibodies",*J. Immunol.* 129: 2739-2743 (1982).

Henderson et al., "Tumor destruction and kinetics of tumor cell death in two experimental mouse tumors following photodynamic therapy", *Cancer Res.*, 45(2):572-576 (1985).

Henderson et al., "Interaction of photodynamic therapy and hyperthermia: tumor response and cell survival studies after treatment of mice in vivo", *Cancer Res.*, 45(12 Pt 1):6071-6077 (1985).

Henderson et al., "Bacteriochlorophyll-a as photosensitizer for photodynamic treatment of transplantable murine tumors", *J. Photochem. Photobiol. B: Biol.* 10:303-313 (1991).

Henderson et al., "An in vivo quantitative structure-activity relationship for a congeneric series of pyropheophorbide derivatives as photosensitizers for photodynamic therapy", *Cancer Res.* 57(18):4000-4007 (1997).

Henderson et al., "How does photodynamic therapy work?" *Photochem Photobiol.* 55(1):145-157 (1992).

Henderson et al., "Aspects of the cellular uptake and retention of hematoporphyrin derivative and their correlation with the biological response to PRT in vitro", *Adv Exp Med Biol.*, 160:129-38 (1983).

Henderson et al., "Studies on the mechanism of tumor destruction by photoradiation therapy", *Prog Clin Biol Res.* 170:601-612 (1984).

Herrera-Ornelas et al., "Photodynamic therapy in patients with colorectal cancer", *Cancer*, 57(3):677-684 (1986).

Ho et al., "Some components of the tumor-localizing fraction of hematoporphyrin derivative", *Photochemistry and Photobiology*, 52(6):1085-1088 (1990).

Ho et al., "Carbon-14 labeling and biological activity of the tumor-localizing derivative of hematoporphyrin", *Photochem Photobiol*. 48(4):445-449 (1988).

Ho et al., "Activity and physicochemical properties of Photofrin", *Photochem Photobiol*. 54(1):83-87 (1991).

IUPAC-IUB Commission on Biochemical Nomenclature (see, Biochem. 11: 942-944 (1972).

Karpovsky et al., "Production of Target-Specific Effector Cells Using Hetero-Cross-Linked Aggregates Containing Anti-Target Cell and Anti-Fcγ", *J. Exp. Med*. 160:1686 (1984).

Kasper et al., "Isolation and Characterization of A Monoclonal Antibody-Resistant Antigenic Mutant of *Toxoplasma Gondii*", *J. Immunol*. 129: 1694-1699 (1982).

Kessel et al., "Photosensitization with bacteriochlorins", *Photochem Photobiol.*, 58(2):200-203 (1993).

Kessel et al., "Photosensitization by diporphyrins joined via methylene bridges", *Photochemistry and Photobiology* 48(6):741-744 (1988).

Kessel et al., "Photosensitization by synthetic diporphyrins and dichlorins in vivo and in vitro", *Photochemistry and Photobiology* 53(4):475-479 (1991).

Khan et al., "An evaluation of photodynamic therapy in the management of cutaneous metastases of breast cancer", *Eur J Cancer*. 29A(12):1686-1690 (1993).

Kher et al., "Mechano and thermoluminescence of gamma-irradiated CaSO4:Dy phosphor.", *Radiat Prot Dosimetry*. 100(1-4):281-284 (2002).

Kozyrev et al., "Thermolysis of vic-dihydroxybacteriochlorins: a new approach for the synthesis of chlorin-chlorin and chlorin-porphyrin dimers", *Org. Lett*. 1(8):1193-1196 (1999).

Lele et al., "Photodynamic therapy in gynecologic malignancies", *Gynecol Oncol*. 34(3):350-352 (1989).

Li et al., "A novel synthetic route to fused propenochlorin and benzochlorin photodynamic therapy probes", *Chem Commun (Camb)*. (11):1172-1173 (2002).

Li et al., "Thermolysis of vic-dihydroxybacteriochlorins: effect of the nature of substrates in directing the formation of chlorin-chlorin dimers with fixed and flexible orientations and their preliminary in vitro photosensitizing efficacy", *J Org Chem*. 68(10):3762-3772 (2003).

Li et al., "A simple and efficient approach for the synthesis of fluorinated and nonfluorinated octaethylporphyrin-based benzochlorins with variable lipophilicity, their in vivo tumor uptake, and the preliminary in vitro photosensitizing efficacy", *J Org Chem*. 66(4):1316-1325 (2001).

Liu, MA et al., "Heteroantibody duplexes target cells for lysis by cytotoxic T lymphocytes",*Proc. Natl. Acad. Sci. USA* 82:8648-8652 (1985).

Lobel et al., "2-[1-hexyloxyethyl]-2-devinyl pyropheophorbide-a (HPPH) in a nude rat glioma model: implications for photodynamic therapy", *Lasers Surg Med*. 29(5):397-405 (2001).

MacDonald et al., "Subcellular localization patterns and their relationship to photodynamic activity of pyropheophorbide-a derivatives", *Photochem Photobiol*. 70(5):789-797 (1999).

Mang et al., "Photobleaching of porphyrins used in photodynamic therapy and implications for therapy", *Photochemistry and Photobiology*, 45(4):501-506 (1987).

Mang et al., "Time and sequence dependent influence of in vitro photodynamic therapy (PDT) survival by hyperthermia", *Photochem Photobiol.*, 42(5):533-540 (1985).

Mang et al., "Fluorescence detection of tumors. Early diagnosis of microscopic lesions in preclinical studies", *Cancer* 71(1):269-276 (1993).

Merrifield et al., "Design and synthesis of antimicrobial peptides", *Ciba Foundation Symposium*, 186:5-20 (1994).

Mettath et al., "DNA interaction and photocleavage properties of porphyrins containing cationic substituents at the peripheral position" *Bioconjugate Chem.*, 10:94-102 (1999).

Mettath et al., "Effect of substituents in directing the formation of benzochlorins and isobacteriochlorins in porphyrin and chlorin systems", *Organic Letters* 1(12):1961-1964 (1999).

Milstein et al., "Hybrid hybridomas and the production of bi-specific monoclonal antibodies",*Immunol. Today* 5:299-305 (1984).

Moesta et al., "Protoporphyrin IX occurs naturally in colorectal cancers and their metastases" *Cancer Research*, 61:991-999 (2001).

Morgan et al., "Comaprison of photodynamic targets in a carcinoma cell line and its mitochondrial DNA-deficient derivative", *Photochemistry and Photobiology*, 71(6):747-757 (2000).

Morrison and Boyd, *Organic Chemistry*, (5th Ed., 1987), Chapter 13, entitled "Aromaticity," pp. 477-497.

Moskal et al., "Operation and photodynamic therapy for pleural mesothelioma: 6-year follow-up", *Ann Thorac Surg.*, 66:1128-1133 (1998).

Nambisan et al., "Intraoperative photodynamic therapy for retroperitoneal sarcomas", *Cancer*, 61(6):1248-1252 (1988).

Niedre et al., "Direct Near-infrared Luminescence Detection of Singlet Oxygen Generated by Photodynamic Therapy in Cell in Vitro and Tissues In Vivo", *Photochemistry and Photobiology*, 75(4):382-391 (2002).

Nogrady, Medicinal Chemistry A Biochemical Approach, Oxford University Press, New York, pp. 388-392 (1985).

North et al., "Viral Inactivation in Blood and Red Cell Concentrates with Benzoporphyrin Derivative", *Blood Cells* 18:129-40 (1992).

Nseyo et al., "Study of factors mediating effect of photodynamic therapy on bladder in canine bladder model", *Urology*, 32(1):41-45 (1988).

Nseyo et al., "Whole bladder photodynamic therapy for transitional cell carcinoma of bladder", *Urology*, 26(3):274-280 (1985).

Nseyo et al., "Photodynamic therapy in the management of resistant lower urinary tract carcinoma", *Cancer* 60:3113-3119 (1987).

Nseyo et al., "Photodynamic therapy (PDT) in the treatment of patients with resistant superficial bladder cancer: a long-term experience", *Journal of Clinical Laser Medicine Surgery*, 16(1):61-68 (1998).

Nseyo et al., "Dihematoporphyrin ether clearance in primate bladders", *The Journal of Urology*, 136:1363-1366 (1986).

Nseyo et al., "Experimental photodynamic treatment of canine bladder", *J Urol.*, 133(2):311-315 (1985).

Paajanen et al., "Proton Relaxation Enhancement of Albumin, Immunoglobulin G, and Fibrinogen Labeled with Gd-DTPA",*Magn. Reson. Med.* 13: 38-43 (1990).

Pandey et al., "Synthesis and photosensitizing activity of a di-porphyrin ether", *Chemical Abstracts*, 109:320 (1988).

Pandey et al., "Synthesis, photophysical properties, in vivo photosensitizing efficacy, and human serum albumin binding properties of some novel bacteriochlorins", *J. Med. Chem.* 40(17):2770-2779 (1997).

Pandey et al., "Chlorin and porphyrin derivatives as potential photosensitizers in photodynamic therapy", *Photochemistry and Photobiology* 53(1):65-72 (1991).

Pandey et al., "Syntheses and photosensitizing activity of porphyrins joined with ester linkages", *Cancer Research* 49:2042-2047 (1989).

Pandey et al., "Evaluation of new benzoporphyrin derivatives with enhanced PDT efficacy", *Photochemistry and Photobiology* 62(4):764-768 (1995).

Pandey et al., "Alkyl ether analogs of chlorophyll-a derivatives: Part 1. Synthesis, photophysical properties and photodynamic efficacy", *Photochemistry and Photobiology* 64(1):194-204 (1996).

Pandey et al., "Porphyrin dimers as photosensitizers in photodynamic therapy", *J. Med. Chem.* 33:2032-2038 (1990).

Pandey et al., "Fast atom bombardment mass spectral analyses of Photofrin II and its synthetic analogs", *Biomedical and Environmental Mass Spectrometry* 19:405-414 (1990).

Pandey et al., "Comparative in vivo sensitizing efficacy of porphyrin and chlorin dimers joined with ester, ether, carbon-carbon or amide bonds" *Journal of Molecular Recognition* 9:118-122 (1996).

Pierce Chemical Co. catalog, pp. O-90 to O-110 (1995, Pierce Chemical Co., 3747 N. Meridian Rd., Rockford III., 61105, U.S.A.).

Polin, R.A. "Monoclonal Antibodies Against Microorganisms", *Eur. J. Clin. Microbiol.*, 3(5): 387-398 (1984).

Potter et al., "The theory of photodynamic therapy dosimetry: consequences of photodestruction of sensitizer", *Photochemistry and Photobiology* 46(1):97-101 (1987).

Potter et al., "Photofrin II levels by in vivo fluorescence photometry", *Prog Clin Biol Res.* 170:177-186 (1984).

Potter et al., "Parabolic quantitative structure-activity relationships and photodynamic therapy: application of a three-compartment model with clearance to the in vivo quantitative structure-activity relationships of a congeneric series of pyropheophorbide derivatives used as photosensitizers for photodynamic therapy", *Photochemistry and Photobiology* 70(5):781-788 (1999).

Prakash, G.K.S. and A.K. Yudin, "Perfluoralkylation with Organosilicon Reagents", *Chem Rev.*, 97:757-786 (1997).

Pykett, "NMR Imaging in Medicine", *Scientific American* 246: 78 (1982).

Rakestraw, et al., "Antibody-targeted photolysis: In vitro studies with Sn(IV) chlorin e6 covalently bound to monoclonal antibodies using a modified dextran carrier", *Proc. Nad. Acad. Sci. USA* 87: 4217-4221 (1990).

Ris et al., "Absence of rhodamine 123-photochemotoxicity in human tumor xenografts", *Lasers Surg Med.* 13(1):40-44 (1993).

Roy et al., "Ceramic-Based Nanoparticles Entrapping Water-Insoluble Photosensitizing Anticancer Drugs: A Novel Drug-Carrier System for Photodynamic Therapy", *J Am Chem Soc.* 125(26):7860-7865 (2003).

Runfola et al., "Photodynamic therapy for residual neoplasms of the perianal skin", *Dis Colon Rectum.* 43(4):499-5002 (2000).

Runge et al., "Paramagnetic Agents for Contrast-Enhanced NMR Imaging: A Review", *Am. J. Radiol.* 141: 1209 (1983).

Rungta et al., "Purpurinimides as photosensitizers: effect of the presence and position of substituents in the in vivo photodynamic efficacy", *Bioorg Med Chem Lett.* 10(13):1463-1466 (2000).

Schuh et al., "Photodynamic therapy for palliation of locally recurrent breast carcinoma", *Journal of Clinical Oncology* 5(11):1766-1770 (1987).

Senge et al., "Comparative Analysis of the Conformations of Symmetrically and Asymmetrically Deca- and Undecasubstituted Porphyrins Bearing Meso-Alkyl or -Aryl Groups", *Inorg. Chem.*, 36:1149-1163 (1997).

Sery et al., "Photoradiation of rabbit ocular malignant melanoma sensitized with hematoporphyrin derivative", *Curr Eye Res.* 3(4):519-528 (1984).

Sharman et al., "Photodynamic therapeutics: basic principles and clinical applications", *Curr. Trends Drug Discovery Today* 4, 507 (1999).

Siegel et al., "Comparative mass spectrometric analyses of Photofrin oligomers by fast atom bombardment mass spectrometry, UV and IR matrix-assisted laser desorption/ionization mass spectrometry, electrospray ionization mass spectrometry and laser desorption/jet-cooling photoionization mass spectrometry", *J Mass Spectrom.* 34(6):661-669 (1999).

Simpson et al., Isolation and partial characterization of the tegumental outer membrane of adult *Schistosome mansoni*,*Parasitology* 83: 163-177 (1981).

Singh et al., "Thiocarbamate linkage as internucleoside bond", *Indian J Biochem Biophys.* 33(5):425-427 (1996).

Smith et al., "Passive immunization of mice against *Schistosoma mansoni* with an IgM monoclonal amtibody",*Parasitology* 84:83-91 (1982).

Smith et al., "Meso Substitution of Chlorophyll Derivatives: Direct Route for Transformation of Bacteriopheophorbides d into Bacteriopheophorbides c", *J. Am. Chem. Soc.* 107: 4946-4954 (1985).

Svaasand et al., "Temperature rise during photoradiation therapy of malignant tumors", *Med Phys.* 10(1):10-17 (1983).

Takita et al., "Intracavitary photodynamic therapy for malignant pleural mesothelioma", *Semin Surg Oncol.* 11:368-371 (1995).

Takita et al., "Operation and intracavitary photodynamic therapy for malignant pleural mesothelioma: a phase II study", *Ann Thorac Surg.* 58(4):995-998 (1994).

Tsuchida et al., "Correlation between site II-specific human serum albumin (HSA) binding affinity and murine in vivo photosensitizing efficacy of some Photofrin components", *Photochemistry and Photobiology* 66(2):224-228 (1997).

Umemura et al., "Recent advances in sonodynamic approach to cancer therapy", *Ultrasonic Sonochemistry* 3: S187-S191 (1996).

Van Lier, J.E. "Photosensitization: Reaction Pathways", *Photobiological Techniques* 216: 85-98 (1991).

Vincent et al., "Photoradiation therapy in advanced carcinoma of the trachea and bronchus", *Chest*, 85(1):29-33 (1984).

Vincent et al., "Hematoporphyrin derivative in the diagnosis and treatment of lung cancer", *Adv Exp Med Biol.* 160:41-46 (1983).

Waldow et al., "Interaction of hyperthermia and photoradiation therapy" *Radiat Res.* 97(2):380-385 (1984).

Waldow et al., "Potentiation of photodynamic therapy by heat: effect of sequence and time interval between treatments in vivo", *Lasers Surg Med.* 5(2):83-94 (1985).

Waldow et al., "Enhanced tumor control following sequential treatments of photodynamic therapy(PDT) and localized microwave hyperthermia in vivo", *Lasers Surg Med.* 4(1):79-85 (1984).

Waldow et al., "Hyperthermic potentiation of photodynamic therapy employing Photofrin I and II: comparison of results using three animal tumor models", *Lasers Surg Med.* 7(1):12-22 (1987).

Weishaupt et al., "Identification of singlet oxygen as the cytotoxic agent in photoinactivation of a murine tumor", *Cancer Res.*, 36(7 PT 1):2326-2329 (1976).

Wilson et al., "The physics of photodynamic therapy," *Phys. Med. Biol.*, 31(4):327-360 (1986).

Wilson et al., "Photodynamic therapy for the treatment of basal cell carcinoma", *Arch Dermatol.* 128:1597-1601 (1992).

Wood et al., "A beam-splitting device for use with fiber-coupled laser light sources for photodynamic therapy", *Photochem Photobiol.*, 76(6):683-685 (2002).

Yoshida et al., "Hybridoma Produces Protective Antibodies Directed Against the Sporozoite Stage of Malaria Parasite", *Science*, 207:71-73 (1980).

Yumita et al., Sonodynamically induced antitumor effect of gallium-porphyrin complex by focused ultrasound on experimental kidney tumor *Cancer Letters* 1,2: 79-86 (1997).

Yumita et al., "The Comination Treatment of Ultrasound and Antitumor Drugs on Yoshida Sarcoma", *Japan J. Hyperthermic Oncology* 3(2):175-182 (1987).

Zheng et al., "A Simple and Short Synthesis of Divinyl Chlorophyll Derivatives", *J Org Chem.* 64:3751-3754 (1999).

Zheng et al., "Synthesis of beta-galactose-conjugated chlorins derived by enyne metathesis as galectin-specific photosensitizers for photodynamic therapy", *J Org Chem.* 66(26):8709-8716 (2001).

Zheng et al., "Synthesis, photophysical properties, tumor uptake, and preliminary in vivo photosensitizing efficacy of a homologous series of 3-(1'-alkyloxy)ethyl-3-devinylpurpurin-18-N-alkylimides with variable lipophilicity", *J Med Chem.* 44:1540-1559 (2001).

Zheng et al., "Photosensitizers related to purpurin-18-N-alkylimides: a comparative in vivo tumoricidal ability to ester versus amide functionalities", *Bioorganic & Medicinal Chemistry Letters*, 10:123-127 (2000).

Zheng et al., "Wittig reactions on photoprotoporphyrin IX: new synthetic models for the special pair of the photosynthetic reaction center", *J Org Chem.* 65(2):543-557 (2000).

Zodda et al., Monoclonal Antibody-Mediated Protection against *Schistosoma mansoni* Infection in Mice, *J. Immunol.* 129: 2326-2328 (1982).

Anderson et al. "Photodynamic therapy for sarcoma pulmonary metastases: a preclinical toxicity study," *Anticancer Res.* 23:3713-3718 (2003).

Certified English Translation of: Fischer, H. et al., "[On the Bromination of the Esters of Mesoisochlorin e4 and Mesochlorin e6]," *Berischte der Deutschen Chemischen* 75:1778-1795 (1942).

Chen et al., "New directions in photodynamic therapy," *ICCP-2. 2nd International Conference on Porphyrins and Phthalocyanines*, Jun. 30-Jul. 5, 2002; Kyoto, Japan: 78 [abstract S-26].

Chen et al., "New technology for deep light distribution in tissue for phototherapy," *Cancer J* 8(2):154-163. (2002).

Chen et al., "Next-generation light delivery system for multitreatment extended-duration photodynamic therapy (MED-PDT)," *Proc SPIE* 2972:161-166 (1997).

Database Crossfire Beilstein, Database Acession No. 4286587 (Reaction ID), for Levinson, E.G. et al., Russ. J. Bioorg. Chem (Engl. Transl.) 21(3):199-203 (1995) in Russian in the :Bioorg. Khim. 21(3):230-234 (1995).

Derwent English Abstract, Accession No. 1996-475153, citing Russian Patent RU 2054944 C, published Feb. 27, 1996, "Production of purpurin-18 for treatment of tumors—comprises extracting vegetable waste with ethanol, oxidative splitting, degreasing and purifying".

Fischer, H. et al., "[On the Bromination of the Esters of Mesoisochlorin $e_4$ and Mesochlorin $e_6$]," *Berischte der Deutschen Chemischen* 75:1778-1795 (1942).

Haslam et al., "Recent Developments in Methods for the Esterification and Protection of the Carboxyl Group," *Tetrahedron* 36: 2409-2433 (1980).

Jones et al. "Photodynamic therapy for patients with advanced non-small-cell carcinoma of the lung," *Clin Lung Cancer*. 3(1):37-41 (2001).

Li et al., "Application of Ruppert's reagent in preparing novel perfluorinated porphyrins, chlorins and bacteriochlorins", *J. Chem. Soc. Perkin Trans* 1, 1785-1787 (1999).

Li et al., "Synthesis, comparative photosensitizing efficacy, human serum albumin (site II) binding ability, and intracellular localization characteristics of novel benzobacteriochlorins derived from vic-dihydroxybacteriochlorins,". *J Med Chem.* 46(25):5349-5359 (2003).

Lusting et al., "A multicenter Phase I safety study of intratumoral photoactivation of talaporfin sodium in patients with refactory solid tumors," *Cancer* 98(8):1767-71 (2003).

Patent Abstract of Japan citing Japanese Patent Application JP 09124652, published May 13, 1997, "Porphyrin Derivative and Use Thereof".

Schmidt-Erfurth et al., "Photodynamic therapy of subfoveal choroidal neovascularization: clinical and angiographic examples," *Graefe's Arch Clin Exp Opthalmol*. 236:365-374 (1998).

Schmidt-Erfurth et al., "Vascular Targeting in Photodyamic Occlusion of Subretinal Vessels," *Opthalmology* 101:1953-1961 (1994).

Smith et al., "Bacteriochlorophylls c from *Chloropseudomonas ethylicum*. Composition and NMR Studies of the Pheophorbide and Derivatives", Am. Chem. Soc., 102(7):2437-2448 (1980).

Zheng et al., "Chlorin-based symmetrical and unsymmetrical dimers with amide linkages: effect of the substituents on photodynamic and photophysical properties," *J. Chem. Soc. Perkins 1*, pp. 3113-3121 (2000).

Zheng et al., "PDT using a novel LED light source and LSII in a rat liver model," *30th Annual Meeting of the American Society for Photobiology*; Jul. 13-17, 2002, Quebec City, Canada. American Society for Photobiology: 33 [abstract 95].

\* cited by examiner

EFFICIENT SYNTHESIS OF PYROPHEOPHORBIDE A AND ITS DERIVATIVES

RELATED APPLICATIONS

Priority is claimed herein under 35 U.S.C. §119(e) to U.S. provisional patent application No. 60/393,617, filed Jul. 2, 2002, to Pandey et al., entitled "EFFICIENT SYNTHESIS OF PYROPHEOPHORBIDE A AND ITS DERIVATIVES." The above-referenced application is incorporated herein by reference in its entirety.

STATEMENT REGARDING FEDERALLY SPONSORED RESEARCH

This invention was made with funding from the National Institute of Health Grant Number NIH CA55792. The United States Government may have certain rights in this invention.

FIELD

Provided herein is a process for the preparation of pyropheophorbide a and its derivatives, including hexyloxy pyropheophorbide a, otherwise known as HPPH. The process involves treating chlorin $e_6$, in the form of its trimethyl ester, with a base, followed by heating to give pyropheophorbide a, which is converted to HPPH by treatment with hexyl alcohol under acidic conditions.

BACKGROUND

Photodynamic therapy (PDT) is relatively a new treatment method for the destruction of tumors. PDT is based on the accumulation in malignant tissue of a photosensitizer after its administration. Subsequent illumination with light of an appropriate wavelength creates a photochemical reaction, a so-called photodynamic effect (photochemical reaction producing singlet oxygen) that results in tumor destruction.

It is well established that both absorption and scattering of light by tissue increases as the wavelength decreases, and that the most effective sensitizers are those that have strong absorption bands between 660–800 nm. In recent years, a series of photosensitizers have been developed related to pyropheophorbide-a and purpurinimides (obtained from purpurin-18) with a variable lipophilicity exhibiting the longer wavelength absorption at 665 and 705 nm (in vivo absorption) respectively.

Historically, preparation of HPPH has required the isolation of methyl pheophorbide a from *Spirulina Algae* by cryogenic fracturing of the cells followed by extraction, chromatographic purification, and recrystallization. See, e.g., U.S. Pat. No. 5,198,460 and references cited therein. The methyl pheophorbide a obtained in this way was then separately subjected to thermal decarboxylation in collidine at reflux temperature. Following this treatment, the resulting methyl pyropheophorbide a was treated with hexyl alcohol and acid to form the hexyl ether moiety. Finally, the methyl ester was removed by saponification to give HPPH. Thus, four rather laborious steps were required in order to obtain HPPH. This procedure works well in the laboratory scale preparation where the final product is required in small amounts. However, the purification of the intermediates at several stages of the synthesis requires column chromatography. Therefore, there is a need for an alternate synthesis of HPPH suitable for large-scale synthesis.

SUMMARY

Provided herein is a synthetic process for the preparation of hexyloxy pyropheophorbide a and related compounds. The process is suitable for large scale (i.e., multigram to multi-kilogram or more) production of such compounds.

The process provided herein affords the desired product in higher yield and/or purity than known processes. Also, the process provided herein avoids the use of chromatographic purification of intermediates and/or desired product.

DETAILED DESCRIPTION

A. Definitions

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

As used herein, "methyl pheophorbide a" refers to:

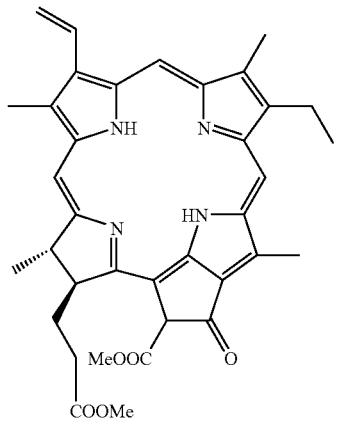

As used herein, "chlorin e6 trimethyl ester" refers to:

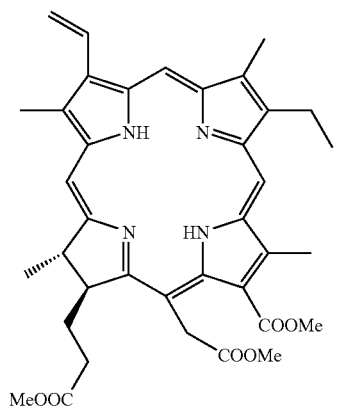

As used herein, an "aromatic solvent" is an organic compound having an aromatic nucleus.

As used herein, "pyropheophorbide a" refers to:

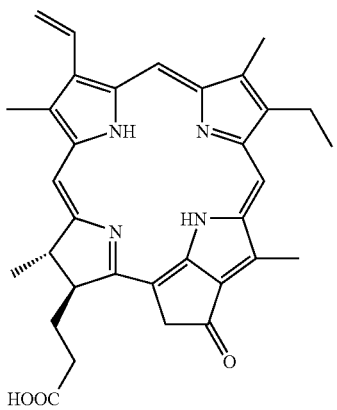

As used herein, a "high boiling aromatic solvent" refers to an aromatic solvent, as defined herein, that has a boiling point high enough to effect decarboxylation of the following compound at reflux:

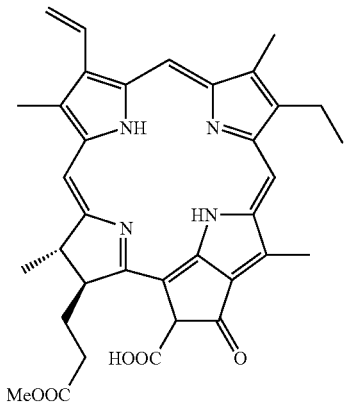

In certain embodiments herein, the boiling point of a high boiling aromatic solvent is greater than 115° C., 120° C., 125° C., 130° C., 135° C., 140° C., 145° C., 150° C., 155° C., 160° C., 165° C. or 170° C.

As used herein, "ether analogs of pyropheophorbide a" refers to compounds of the general formula:

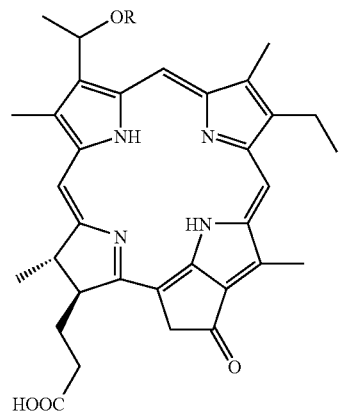

where R is alkyl, alkenyl, alkynyl, cycloalkyl, heterocyclyl, aryl or heteroaryl, and is unsubstituted or substituted with one or more substituents, in one embodiment one to five substituents, in another embodiment one, two or three substituents, each independently selected from halo, pseudohalo, alkyl, alkenyl, alkynyl, cycloalkyl, heterocyclyl, aryl, heteroaryl, hydroxy, alkoxy, aryloxy, carboxy, aralkoxy, sulfones, amines, amides and sulfonamides.

As used herein, "purpurin-18" is:

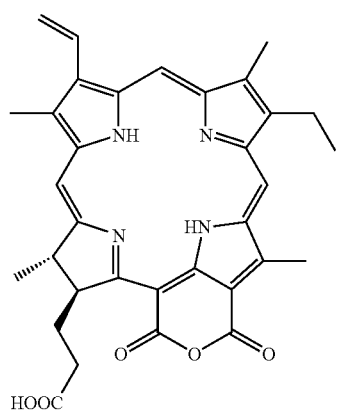

As used herein, a "base" is an inorganic or organic compound sufficiently basic to effect a Dieckmann condensation. In certain embodiments, the base is an organic compound. In other embodiments, the base has a pKa of the corresponding protonated form of less than about 15, 10, 8 or 5, relative to water.

As used herein, "ether analogs of pururin-18" refers to compounds of the general formula:

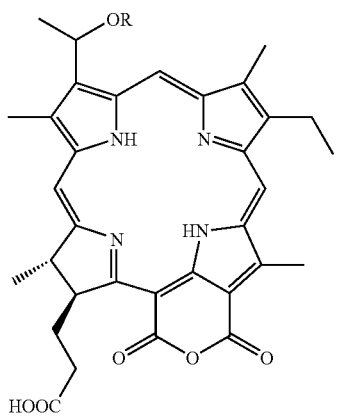

where R is alkyl, alkenyl, alkynyl, cycloalkyl, heterocyclyl, aryl, or heteroaryl, and is unsubstituted or substituted with one or more substituents, in one embodiment one to five substituents, in another embodiment one, two or three substituents, each independently selected from halo, pseudohalo, alkyl, alkenyl, alkynyl, cycloalkyl, heterocyclyl, aryl, heteroaryl, hydroxy, alkoxy, aryloxy, carboxy, aralkoxy, sulfones, amines, amides and sulfonamides.

As used herein, a "purpurinimide" is a compound of the general formula:

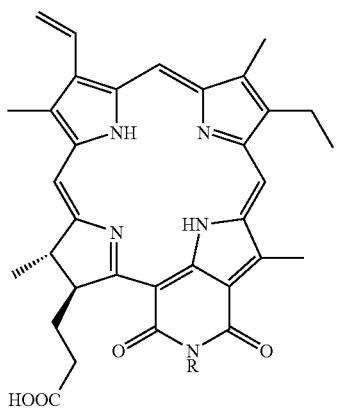

where R is alkyl, alkenyl, alkynyl, cycloalkyl, heterocyclyl, aryl or heteroaryl, and is unsubstituted or substituted with one or more substituents, in one embodiment one to five substituents, in another embodiment one, two or three substituents, each independently selected from halo, pseudohalo, alkyl, alkenyl, alkynyl, cycloalkyl, heterocyclyl, aryl, heteroaryl, hydroxy, alkoxy, aryloxy, carboxy, aralkoxy, sulfones, amines, amides and sulfonamides.

As used herein, "ether analogs of purpurinimides" refers to compounds of the general formula:

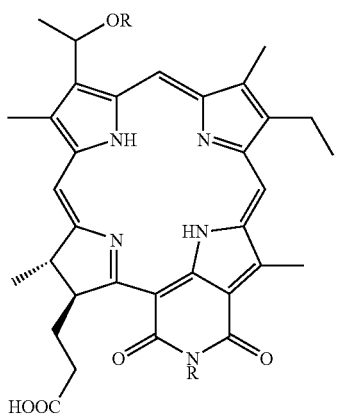

where R is independantly alkyl, alkenyl, alkynyl, cycloalkyl, heterocyclyl, aryl or heteroaryl, and is unsubstituted or substituted with one or more substituents, in one embodiment one to five substituents, in another embodiment one, two or three substituents, each independently selected from halo, pseudohalo, alkyl, alkenyl, alkynyl, cycloalkyl, heterocyclyl, aryl, heteroaryl, hydroxy, alkoxy, aryloxy, carboxy, aralkoxy, sulfones, amines, amides and sulfonamides.

As used herein, an "acid" is an inorganic or organic compound of sufficient acidity to effect addition of an alcohol to a vinyl group. In one embodiment, an acid is an inorganic compound. In another embodiment, an acid has sufficient acidity to effect addition of an alcohol to a vinyl group directly attached to an aromatic porphyrin nucleus.

As used herein, the term "porphyrin" refers to a cyclic structure typically composed of four pyrrole rings, and refers to a porphyrin or porphyrin derivative. Such derivatives include porphyrins with extra rings ortho-fused, or ortho-perifused, to the porphyrin nucleus, porphyrins having a replacement of one or more carbon atoms of the porphyrin ring by an atom of another element (skeletal replacement), derivatives having a replacement of a nitrogen atom of the porphyrin ring by an atom of another element (skeletal replacement of nitrogen), derivatives having substituents other than hydrogen located at the peripheral (meso-, β-) or core atoms of the porphyrin, derivatives with saturation of one or more bonds of the porphyrin (hydroporphyrins, e.g., chlorins, bacteriochlorins, isobacteriochlorins, decahydroporphyrins, corphins, pyrrocorphins, etc.), derivatives obtained by coordination of one or more metals to one or more porphyrin atoms (metalloporphyrins), derivatives having one or more atoms, including pyrrolic and pyrromethenyl units, inserted in the porphyrin ring (expanded porphyrins), derivatives having one or more groups removed from the porphyrin ring (contracted porphyrins, e.g., corrin, corrole) and combinations of the foregoing derivatives (e.g phthalocyanines, porphyrazines, naphthalocyanines, subphthalocyanines, and porphyrin isomers).

As used herein, "chlorin" refers to a class of porphyrin derivatives having a cyclic structure typically composed of four pyrrole rings having one partially saturated pyrrole ring, such as the basic chromophore of chlorophyll.

As used herein, alkyl, alkenyl and alkynyl carbon chains, if not specified, contain from 1 to 20 carbons, or 1 or 2 to 16 carbons, and are straight or branched. Alkenyl carbon chains of from 2 to 20 carbons, in certain embodiments, contain 1 to 8 double bonds and alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-pentyl, isohexyl, allyl (propenyl) and propargyl (propynyl). As used herein, lower alkyl, lower alkenyl, and lower alkynyl refer to carbon chains having from about 1 or about 2 carbons up to about 8 carbons.

As used herein, halogen refers to one of the electronegative elements of group VIIA of the periodic table (fluorine, chlorine, bromine, iodine, astatine).

As used herein, "hydroxy group" generally refers to a hydroxyl group having the formula —OH.

As used herein, "carboxy" generally refers to the radical —C(O)OH.

As used herein, "ester group" generally refers to a substituent of the general formula —C—O—O—$R^1$ where $R^1$ may be either aliphatic or aromatic.

As used herein, "aromatic group" generally refers to a ring structure having cyclic clouds of delocalized π electrons above and below the plane of the molecule, where the π clouds contain (4n+2) π electrons. A further discussion of aromaticity is found in Morrison and Boyd, *Organic Chemistry*, (5th Ed., 1987), Chapter 13, entitled "Aromaticity," pages 477–497, incorporated herein by reference.

As used herein, "amide group" generally refers to the group —C(O)NRR where each R is independently aliphatic or aromatic.

As used herein, "amine group" has the general formula —NRR, where each R is independently any alkyl or aryl group.

As used herein, "cycloalkyl" refers to a saturated mono- or multi-cyclic ring system, in certain embodiments of 3 to 20 carbon atoms, in other embodiments of 3 to 10 carbon atoms. The ring systems of the cycloalkyl groups may be composed of one ring or two or more rings which may be joined together in a fused, bridged or spiro-connected fashion.

As used herein, "aryl" refers to aromatic monocyclic or multicyclic groups containing from 6 to 19 carbon atoms. Aryl groups include, but are not limited to groups such as unsubstituted or substituted fluorenyl, unsubstituted or substituted phenyl, and unsubstituted or substituted naphthyl.

As used herein, "heteroaryl" and "heteroaromatic group" refers to a monocyclic or multicyclic aromatic ring system, in certain embodiments, of about 5 to about 20 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl and isoquinolinyl.

As used herein, "heterocyclyl" refers to a monocyclic or multicyclic non-aromatic ring system, in one embodiment of 3 to 20 members, in another embodiment of 4 to 10 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, or the nitrogen may be quaternized to form an ammonium group where the substituents are selected as above.

As used herein, "aralkyl" refers to an alkyl group in which one of the hydrogen atoms of the alkyl is replaced by an aryl group.

As used herein, "heteroaralkyl" refers to an alkyl group in which one of the hydrogen atoms of the alkyl is replaced by a heteroaryl group.

As used herein, "halo", "halogen" or "halide" refers to F, Cl, Br or I.

As used herein, pseudohalides or pseudohalo groups are groups that behave substantially similar to halides. Such compounds can be used in the same manner and treated in the same manner as halides. Pseudohalides include, but are not limited to, cyanide, cyanate, thiocyanate, selenocyanate, trifluoromethoxy, and azide.

All chemical compounds include both the (+) and (−) stereoisomers, as well as either the (+) or (−) stereoisomer, and also all diastereomers, rotamers and geometric isomers.

B. Process for Preparing Pyropheophorbide a and its Derivatives

The process provided herein, depicted below, avoids a number of shortcomings of the prior art by resorting to another source as the raw material. Chlorin $e_6$ trimethyl ester undergoes a Dieckmann Condensation to form the additional exocyclic ring, sometimes called an "E-ring", which is present in the pheophorbides, and chlorophyll itself for that matter. See, e.g., Schaefer, J. P.; Bloomfield, J. J. Org. React. 1967, 15, 1–203; and Davis, B. R.; Garrett, P. J. Comp. Org. Syn. 1991, 2, 806–829. This reaction has traditionally been performed in aromatic solvents, originally benzene, but later toluene and others for safety reasons. In the case of chlorin $e_6$ and compounds like it, pyridine has been used for this purpose. See, e.g., Smith, K. M.; Bisset, G. M. F.; Bushell, M. J. J. Org. Chem. 1980, 45, 2218–2224. These workers did not use chlorin $e_6$ itself, but a similar compound in which a methyl group substituent was present at position 5, the δ "meso" position.

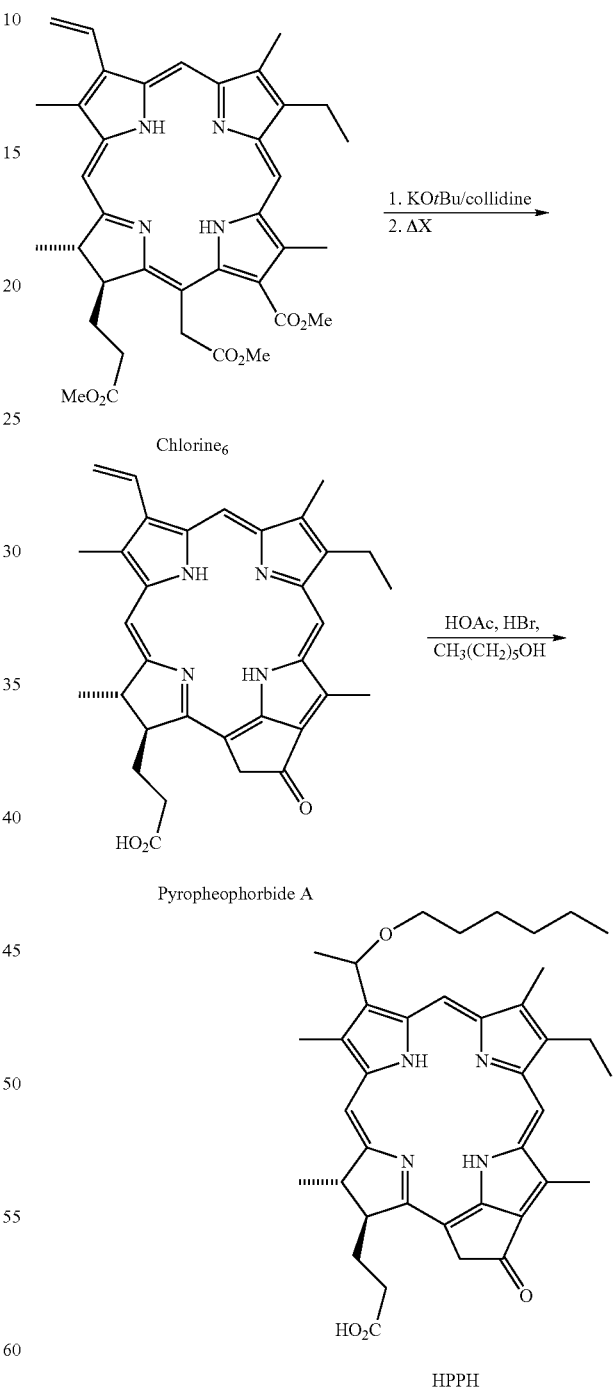

In order to improve the performance of this reaction, the pyridine was replaced with a more substituted analog in order to raise the boiling point of the reaction mixture. Thus, collidine, also called sym-collidine (for symmetrical, see below) or 2,4,6-trimethylpyridine, was used. Other basic aromatic solvents, including but not limited to 2,6-lutidine, could also be used. In this way the temperature of reflux of the reaction mixture is altered—the boiling point of pyridine is 115° C., while that of collidine is 172° C. By raising the temperature of the reaction mixture after completion of the Dieckmann Condensation, it is possible to bring about the subsequent thermal decarboxylation without any intervening purification or unnecessary manipulation of the reaction mixture. As a further benefit, it was found that, under the strongly basic conditions employed to carry out the Dieckmann Condensation, the methyl ester of the pheophorbide system also undergoes cleavage, thus accomplishing three chemical transformations in a single treatment.

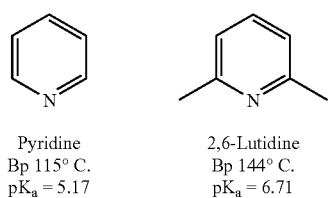

| Pyridine | 2,6-Lutidine | sym-Collidine |
| Bp 115° C. | Bp 144° C. | Bp 172° C. |
| p$K_a$ = 5.17 | p$K_a$ = 6.71 | p$K_a$ = 7.43 |

Basic Aromatic Solvents

The pheophorbide a obtained in this way need only be converted to its hexyl ether in order to produce HPPH. This can be done in much the same way as it was done in the older synthesis, giving an overall two-pot preparation of this product.

Since many other compounds can also be obtained from pyropheophorbide a (see below), this new process affords greatly simplified access to all such compounds. These compounds include purpurin-18 and its derivatives, especially the ethers made from the vinyl group in an analogous manner to the hexyl ether in HPPH, and the purpurinimide series. In these examples, one would omit the high temperature treatment and thermal decarboxylation in order to retain the carboxyl group for the construction of the expanded E-ring used in these systems.

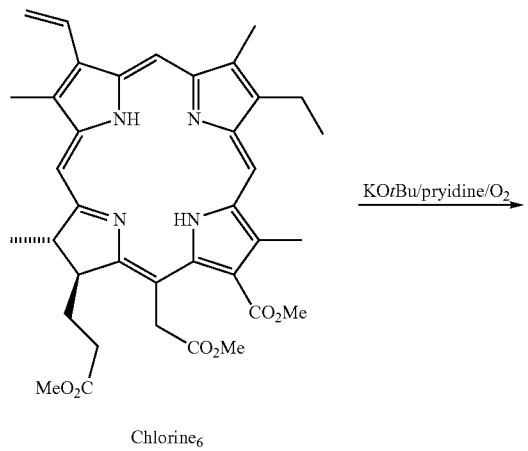

Chlorine$_6$

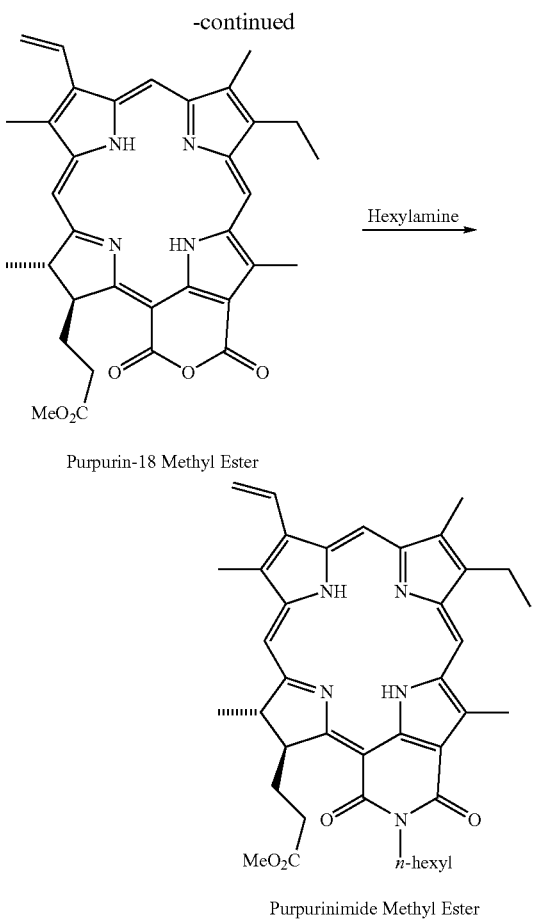

Purpurin-18 Methyl Ester

Purpurinimide Methyl Ester

The following examples are included for illustrative purposes only and are not intended to limit the scope of the subject matter claimed herein.

EXAMPLE 1

Preparation of Pyropheophorbide-a

Chlorin e$_6$ trimethyl ester (350 mg) was dissolved in dry 2,4,6-collidine (30 mL) and then carefully degassed with nitrogen at 50° C. under vacuum. Potassium tert-butoxide (Aldrich, 5.0 mL, 1 M) was added. The initial bright green color immediately turned orange and the reaction mixture was left stirring at room temperature for 20 min. It was then quenched with degassed glacial acetic acid (10 mL). The flask was then connected to a small distillation assembly (condenser, receiving head and a flask), the acetic acid along with a small amount of collidine (5 mL) were removed under high vacuum. The distillation assembly was dismantled and fresh collidine (15 mL) was added. The reaction flask was then connected to a condenser, and the reaction mixture was heated at reflux under nitrogen for 2 hours. The solvent was removed under high vacuum. The residue so obtained was re-dissolved in dichloromethane (100 mL), washed with water (2×100 mL) and dried over anhydrous sodium sulfate. Evaporation of the solvent gave pyropheophorbide-a (as carboxylic acid) in 85% yield after crystallization. $^1$H NMR (CDCl$_3$, δ ppm): 9.35 and 9.15 and 8.50 (each s, 1H, meso H); 7.80 (m, 1H, CH=CH$_2$); 6.25, 6.10 (each d, 1H, CH—CH$_2$); 5.22 (dd, 2H, —CH$_2$, exocyclic ring); 4.41 (q, 1H, 18H); 4.28 (d, 1H, 17-H); 3.75 (q, 2H, CH$_2$CH$_3$ merged with one of the ring CH$_3$); 3.62, 3.35 and 3.10 (each s, 3H, ring CH$_3$); 2.80–2.10 (several m, CH$_2$CH$_2$CO$_2$H); 1.80 (d, 3H, 18-CH$_3$): 1.60 (t, 3H, CH$_2$CH$_3$); −1.78 (each s, 1H, NH).

EXAMPLE 2

3-Devinyl-3-(1'-hexyloxy)ethyl-pyropheophorbide-a (HPPH)

Pyropheophorbide-a (100 mg) was taken in a 50 mL round bottom flask and 30% HBr/HOAc (Aldrich, 2.0 mL) was added. The reaction mixture was stirred at room temperature for 2 hour and the solvent was removed under high vacuum (bath temperature was maintained at 30–40° C.). It was re-dissolved in dry dichloromethane (10 mL). Hexanol (2.00 mL), potassium carbonate (200 mg) were added, and the reaction mixture was stirred at room temperature for 45 min under nitrogen atmosphere. It was poured in water (100 mL), extracted with dichloromethane. The organic layer was washed with water and dried over anhydrous sodium sulfate. Evaporation of the solvent gave a residue that was crystallized from dichloromethane/hexane in 71% yield; $^1$H NMR (CDCl$_3$, δ ppm): 9.77 and 9.52 8.50 (s, 1H, meso-H); 5.90 [q, 1H, CH(o-hexyl)-CH$_3$]; 5.22 (dd, 2H, 2H, exocyclic ring); 4.41 (q, 1H, 18H); 4.28 (d, 1H, 17-H); 3.75 (q, 2H, CH$_2$CH$_3$); 3.62, 3.25 and 3.20 (each s, 3H, ring CH$_3$); 2.10 (3H, CHCH$_3$); 1.80 (d, 3H, 18-CH$_3$): 1.75 (t, 3H, CH$_2$CH$_3$); 2.75–2.12 (several m, CH$_2$CH$_2$CO$_2$H); 0.76–1.30 [several m, 10H, (CH$_2$)$_5$] 0.43 and −1.78 (each s, 1H, NH). Mass calculated for: C$_{39}$H$_{48}$N$_4$O$_4$: 636. Found: 637 (M+1).

EXAMPLE 3

Preparation of Purpurin-18 methyl ester

Chlorin e$_6$ trimethyl ester (175 mg) was dissolved in pyridine (15 mL) and the reaction temperature was maintained at 50° C. A slow stream of air was passed through the solution and potassium tert-butoxide (Aldrich, 2.5 mL, 1.0 M) was added. The reaction mixture was stirred at room temperature for 20 min. It was the quenched with glacial acetic acid (5 mL), poured in water, extracted with dichloromethane (2×100 mL). The dichloromethane layer was washed with 2 M HCl (50 mL), then washed with water again. The organic layer was separated and dried over anhydrous sodium sulfate. The residue obtained after evaporating the solvent was re-dissolved in dichloromethane, treated with diazomethane, purified by silica column chromatography, eluting with 2% acetone in dichloromethane and crystallized from dichloromethane/hexane. Yield 80%; $^1$H NMR (CDCl$_3$, δ ppm): 9.60, 9.35 and 8.60 (each s, 1H, meso-H); 7.90 (m, 1H, CH=CH$_2$); 6.30 and 6.20 (each d, 1H, CH=CH$_2$); 5.12 (d, 1H, 17-H); 4.40 (q, 1H, 18-H); 3.75 (s, 3H, CO$_2$CH$_3$); 3.65 (q, 2H, —CH$_2$CH$_3$); 3.60, 3.30 and 3.15 (each s, 3H, ring CH$_3$); 2.80–1.90 (several m, —CH$_2$CH$_2$CO$_2$CH$_3$); 1.75 (d, 3h, 18-CH$_3$); 1.60 (t, 3H, —CH$_2$CH$_3$); 0.20 and −0.90 (each br s, 1H, NH).

Since modifications will be apparent to those of skill in this art, it is intended that this invention be limited only by the scope of the appended claims.

What is claimed is:

1. A process for the preparation of methyl pheophorbide-a, comprising treating chorin e6 trimethyl ester with a base in an aromatic solvent having a boiling point at least as high as 144° C., the boiling point of 2,6-lutidine.

2. A process for the preparation of methyl pheophorbide-a, comprising:
   (a) treating chorin e6 trimethyl ester with a base in an aromatic solvent having a boiling point at least as high as 144° C., the boiling point of 2,6-lutidine to give methyl pheophorbide-a; and
   (b) without isolating the methyl pheophobide-a from the resulting reaction mixture, heating the methyl pheophorbide-a to a temperature sufficient to effect decarboxylation and saponification of the methyl pheophorbide-a.

3. A process for the preparation of ether analogs of pyropheophorbide-a comprising:
   (a) treating chorin e6 trimethyl ester with a base in an aromatic solvent having a boiling point at least as high as 144° C., the boiling point of 2,6-lutidine to give methyl pheophorbide-a;
   (b) without isolating the methyl pheophobide-a from the resulting reaction mixture, heating the methyl pheophorbide-a to a temperature sufficient to effect decarboxylation and saponification of the methyl pheophorbide-a to give pheophorbide-a; and
   (c) treating the pyropheophorbide-a with an acid, followed by an alcohol under basic conditions to effect addition of the alcohol across a vinyl group.

4. The process of claim 3, wherein the alcohol is 1-hexanol (n-hexyl alcohol) to obtain 3-devinyl-3-(hexyloxy) ethyl-pyropheophorbide-a (HPPH).

5. A process for the preparation of purpurin-18, comprising:
   (a) treating chlorin e$_6$ trimethyl ester with a base in an aromatic solvent in the presence of air to give purpurin-18 having a —CH$_2$CH$_2$COOH group.

6. A process for the preparation of purpurinimides, comprising:
   (a) treating chlorin e$_6$ trimethyl ester with a base in an aromatic solvent in the presence of air to give purpurin-18 having a —CH$_2$CH$_2$COOH group;
   (b) esterifying the —CH$_2$CH$_2$COOH group to obtain purpurin-18 ester; and
   (c) treating the esterified purpurin-18 with a primary amine.

7. A process for the preparation of ether analogs of purpurinimides, comprising:
   (a) treating chlorin e$_6$ trimethyl ester with a base in an aromatic solvent in the presence of air to give purpurin-18 having a —CH$_2$CH$_2$COOH group;
   (b) esterifying the —CH$_2$CH$_2$COOH group to obtain purpurin-18 ester;
   (c) treating the esterified purpurin-18 ester with a primary amine; and
   (d) treating the resulting purpurinimide with an acid, followed by an alcohol under basic conditions.

8. A process for the preparation of purpurin-18 ester, comprising:
   (a) treating chlorin e$_6$ trimethyl ester with a base in an aromatic solvent in the presence of air to give purpurin-18 having a —CH$_2$CH$_2$COOH group; and
   (b) esterifying the —CH$_2$CH$_2$COOH group.

9. A process for the preparation of ether analogs of purpurin-18, comprising:
   treating the esterified purpurin-18 obtained by the steps of claim 8 with an acid, followed by treating with an alcohol under basic conditions.

10. The method of claim 8 where the group is esterified using diazomethane to obtain purpurin 18 methyl ester.

11. The method of claim 2 where the aromatic solvent is sym-collidine.

* * * * *

UNITED STATES PATENT AND TRADEMARK OFFICE
CERTIFICATE OF CORRECTION

PATENT NO. : 7,053,210 B2
APPLICATION NO. : 10/613474
DATED : May 30, 2006
INVENTOR(S) : Ravindra K. Pandey et al.

It is certified that error appears in the above-identified patent and that said Letters Patent is hereby corrected as shown below:

Col. 12, line 27, in Claim 5, delete "(a)".

Signed and Sealed this

Twenty-fifth Day of March, 2008

JON W. DUDAS
*Director of the United States Patent and Trademark Office*